United States Patent
Enmanji et al.

(10) Patent No.: US 6,319,440 B1
(45) Date of Patent: Nov. 20, 2001

(54) DEODORANT MATERIAL

(75) Inventors: Koe Enmanji; Itsuo Nishiyama; Kenzo Takahashi, all of Amagasaki (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 08/190,569

(22) Filed: Feb. 2, 1994

Related U.S. Application Data

(62) Division of application No. 07/726,171, filed on Jul. 5, 1991, now abandoned.

(30) Foreign Application Priority Data

Sep. 18, 1990 (JP) ...................................... 2-250493
Sep. 26, 1990 (JP) ...................................... 2-259334

(51) Int. Cl.⁷ .................................................. C04B 40/00
(52) U.S. Cl. ............................................ 264/82; 428/389
(58) Field of Search ................................... 428/389, 367, 428/408, 381, 375; 264/29.2, 82; 423/367, 375, 394, 389; 424/76.1, 76.21, 489, 650, 637

(56) References Cited

U.S. PATENT DOCUMENTS

| | | | |
|---|---|---|---|
| 4,210,628 | * | 7/1980 | Ninomiya et al. .................. 423/239 |
| 4,259,397 | * | 3/1981 | Saito et al. ........................... 428/367 |
| 4,459,332 | * | 7/1984 | Giglia .................................... 428/367 |
| 4,460,650 | * | 7/1984 | Ogawa et al. . |
| 4,536,448 | * | 8/1985 | Ogawa et al. . |
| 4,906,462 | * | 3/1990 | Miki et al. . |
| 4,919,925 | * | 4/1990 | Ueda et al. ........................... 424/76.1 |
| 4,959,207 | * | 9/1990 | Ueda et al. . |
| 4,983,441 | * | 1/1991 | Miki et al. . |

FOREIGN PATENT DOCUMENTS

| | | | |
|---|---|---|---|
| 6234565 | | 2/1987 | (JP) . |
| 3084555 | * | 4/1988 | (JP) ..................................... 424/76.1 |
| 2052660 | * | 2/1990 | (JP) ..................................... 424/76.1 |
| 3098642 | * | 4/1991 | (JP) ..................................... 424/76.1 |
| 3085167 | * | 4/1988 | (JP) ..................................... 428/367 |
| 2084527 | * | 3/1990 | (JP) ..................................... 428/367 |

OTHER PUBLICATIONS

Gendai Kagaku, Sep. 1987, pp. 12–13 and pp. 18–22, Dec. 1987.

* cited by examiner

*Primary Examiner*—Merrick Dixon
(74) *Attorney, Agent, or Firm*—Oblon, Spivak, McClelland, Maier & Neustadt, P.C.

(57) ABSTRACT

A deodorant material which comprises, as a carrier, granular or fibrous active carbon treated by either oxidizing treatment or acid-attaching treatment, or polystyrene sulfonic acid, and a cupric ion supported on the carrier.

2 Claims, 3 Drawing Sheets

DEODORANT MATERIAL

This application is a Division of application Ser. No. 07/726,171, filed on Jul. 5, 1991, now abandoned.

BACKGROUND OF THE INVENTION

1. Field of the Invention

The present invention relates to a deodorant material for deodorizing bad odor.

2. Discussion of Background

FIG. 1 is a structural view showing a conventional active carbon. FIG. 2 is a structural view showing a conventional deodorant material supporting cupric ion. In these Figures, 22 is active carbon, 21 is a micropore, 31 is a cellulose fiber, 32 is a OH residual group of cellulose and 33 is cupric ion.

Now, deodorizing mechanism will be described. The active carbon physically adsorbs bad odor molecules existing in air flow with its micropores to conduct deodorization. The cupric ion reacts with bad odor molecules such as $H_2S$ as described in the following scheme to conduct deodorization.

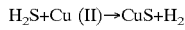

Japanese Unexamined Patent Publication No. 34565/1987 discloses a method wherein cupric ion is attached to active carbon.

Since the conventional deodorant material using the active carbon is constituted as described above, there are drawbacks that when the micropore is saturated with the adsorbed bad odor molecules, the deodorization is no more conducted and the lifetime of the deodorant material is short. Since the reaction rate of the deodorization by use of the cupric ion is low, it is difficult to apply it to an air cleaner which treats a large amount of air. In a method wherein the cupric ion is directly attached to the active carbon, there are drawbacks that the adsorptive sites for the cupric ions on the active carbon are few and that, if a large amount of the cupric ions are supported on the active carbon to improve deodorizing properties, the micropores of the active carbon are filled with copper salts and the deodorizing properties are contrarily lowered.

The present invention is made to solve the above drawbacks. An object of the present invention is to obtain a deodorant material having high efficiency and long lifetime.

SUMMARY OF THE INVENTION

The deodorant material of the present invention is a deodorant material which comprises, as a carrier, granular or fibrous active carbon treated by either oxidizing treatment or acid-attaching treatment, or polystyrene sulfonic acid, and a cupric ion supported on the carrier.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The active carbon, used as a carrier, treated by the oxidizing treatment or the acid-attaching treatment has a large number of active groups such as —CO, —COOH or —$SO_3H$. The cupric ions can be attached to the active carbon in an amount of 100 times the amount an untreated active carbon can. Accordingly, not only the deodorizing performance can be improved, but also the lifetime is greatly extended.

It is preferable to use an acid for the acid-attaching treatment within the range of from 1–10 weight %.

Figure 1:
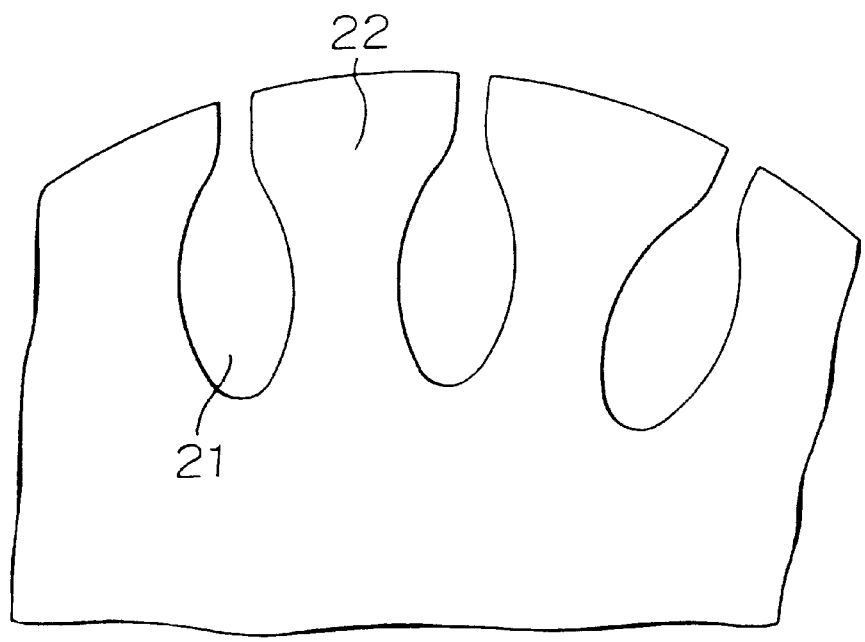
FIG. 1 is a structural view showing an active carbon for a conventional deodorant material.
Figure 2:
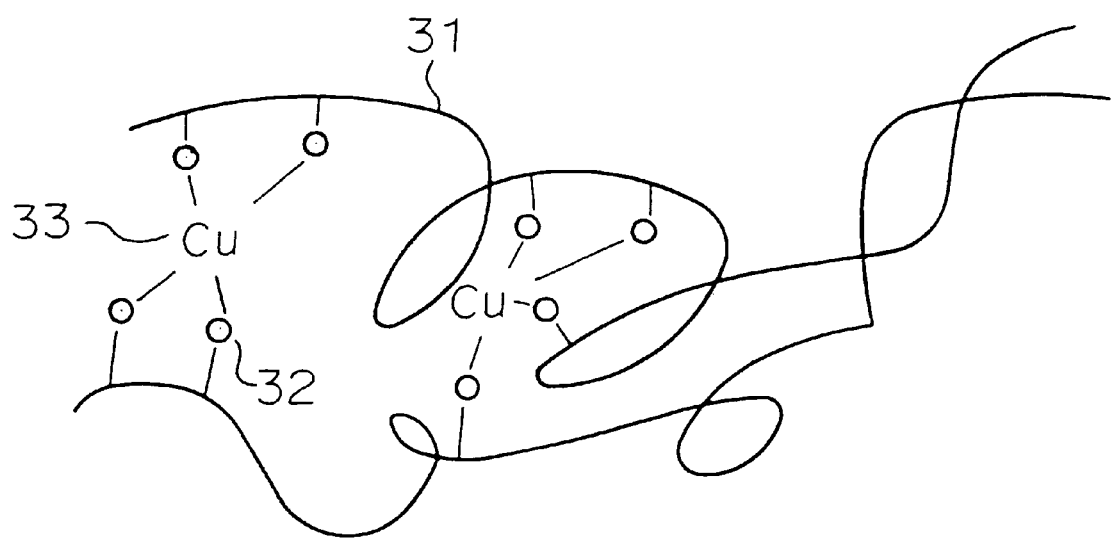
FIG. 2 is a structural view showing a conventional deodorant material supporting cupric ion.
Figure 3:
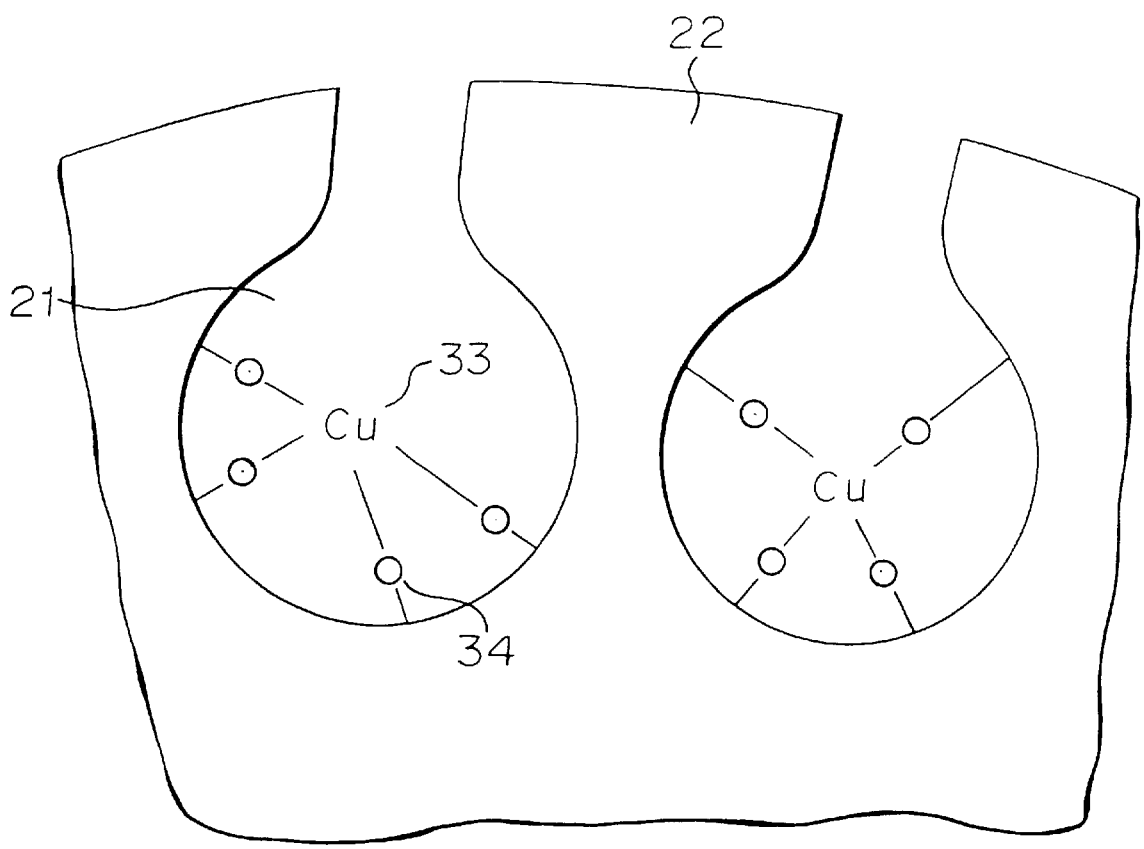
FIG. 3 is a structural view showing a deodorant material of an example of the present invention.

FIG. 3 is a structural view showing a deodorant material for an example of the present invention. In this Figure, 21 is a micropore, 22 is active carbon, 34 is an active group obtained by subjecting the active carbon to the oxidizing treatment or the acid-attaching treatment, and 33 is cupric ion.

Bad odor molecules such as $H_2S$ react with cupric ions attached to the micropores 21 of the active carbon as shown in the following scheme to conduct deodorization of $H_2S$.

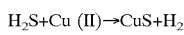

Since the untreated active carbon conventionally used has a small number of the active groups, the site to which the cupric ion is attached is few. Accordingly the attached amount of the cupric ion is small and the effect of expanding lifetime is also small. The oxidized active carbon or the acid-attached active carbon has a large number of active groups and thus the attached amount of the cupric ion become larger to improve greatly the effect of expanding lifetime.

The cupric ion is supported in an amount of preferably from 0.01 to 1 mol per mol of the oxidized active carbon or the acid-attaching treated active carbon.

When polystyrene sulfonic acid is used as a carrier, the cupric ion supported thereon forms a coordinate bond with the polystyrene sulfonic acid, and thus the electrodensity on the $dx^2-y^2$ orbit of the cupric ion is lowered to facilitate the oxidization of bad odor substances.

The cupric ion is supported in an amount of preferably from 0.01 to 1 mol per mol of polystyrene sulfonic acid.

Obviously, numerous modifications and variations of the present invention are possible in light of the above teachings. It is therefore to be understood that within the scope of the appended claims, the invention may be practiced otherwise than as specifically described herein.

EXAMPLE 1

1.6 parts by weight of copper sulfate was dissolved in 100 parts by weight of water. 0.5 part by weight of an oxidized active carbon (trade name: Rynobeth FN-150PSS-10, produced by Kansai Tar Products Company) was immersed in the solution and then well squeezed, followed by drying in an oven at 100° C. for 1 hour to obtain a deodorant material of an Example of the present invention. $H_2S$ gas with a concentration of 2000 ppb was blown through the deodorant material at a rate of 100 l/min. The deodorizing efficiency represented by the following formula was 99.9%.

(concentration at an inlet−concentration at an outlet)/concentration at an inlet The time until the deodorizing efficiency was lowered to 80% was 240 minutes.

EXAMPLE 2

0.5 part by weight of an active carbon fiber (trade name: Finegard, produced by Toho Rayon Company) was heated in 100 parts by weight of a concentrated sulfuric acid at 130° C. for 8 hours to obtain an acid-attached active carbon fiber. After washing with water, the fiber was immersed in a solution of one part by weight of copper sulfate dissolved in 100 parts by weight of water and then dried at room temperature for one night to obtain a deodorant material of another Example of the present invention. When methyl mercaptan gas with a concentration of 2000 ppb was blown through the deodorant material at a rate of 100 l/min., the deodorizing efficiency was 98%. The time until the deodorizing efficiency was lowered to 80% was 350 minutes.

Compartive Example 1

5 parts by weight of copper sulfate was dissolved in 100 parts by weight of water. 0.5 part by weight of an active carbon fiber (trade name: Finegard, produced by Toho Rayon Company) was immersed in the solution and then well squeezed, followed by drying in an oven at 100° C. for 1 hour to obtain a deodorant material. $H_2S$ gas with a concentration of 500 ppb was blown through the above treated active carbon at a rate of 150 l/min. The deodorizing efficiency was 90%. The time until the deodorizing efficiency was lowered to 80% was 35 minutes.

Comparative Example 2

$H_2S$ gas having a concentration of 500 ppm was blown through an active carbon fiber (trade name: Finegard, produced by Toho Rayon Company). The deodorizing efficiency was 87%. The time until the deodorizing efficiency was lowered to 80% was 5 minutes.

EXAMPLE 3

Figure 4:
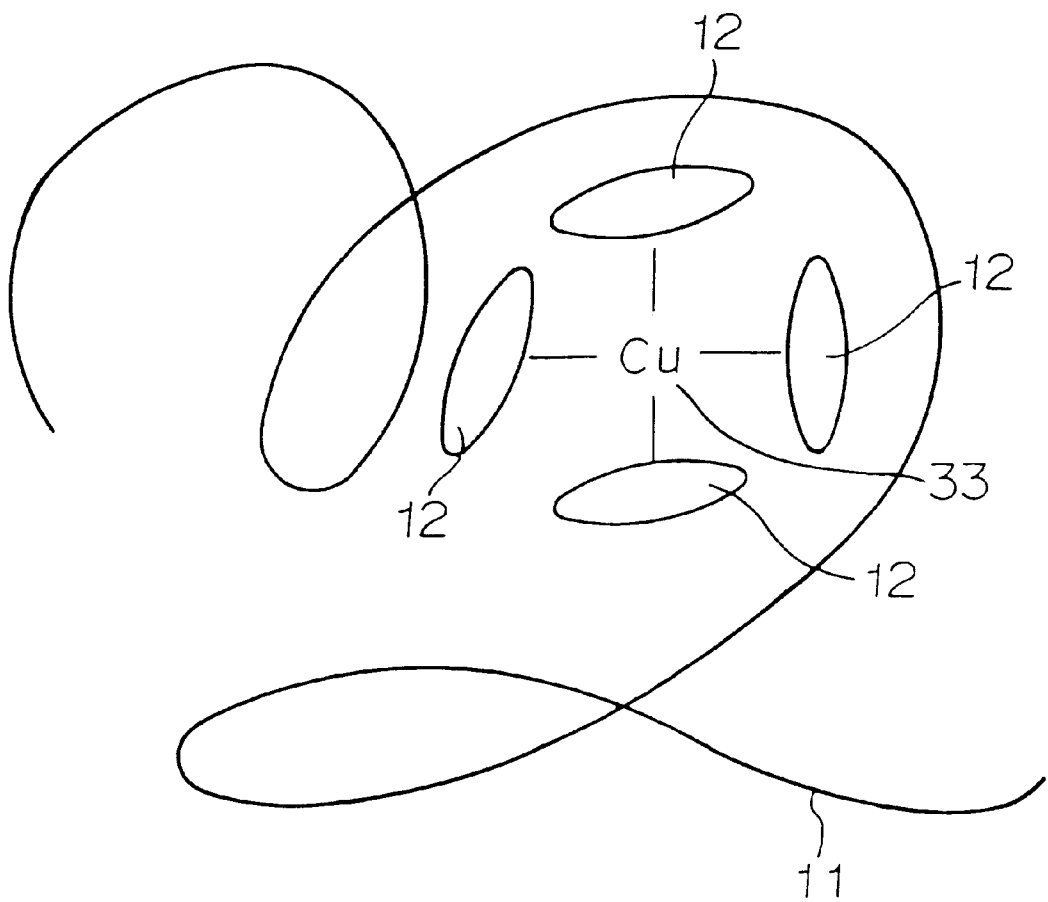
FIG. 4 is a conceptional view showing a deodorant material of another example of the present invention.

In FIG. 4, 11 is a cellulose fiber, 12 is polystyrene sulfonic acid (PSS) and 33 is cupric ion.

Bad odor substances such as $H_2S$ are completely decomposed by a reaction shown below.

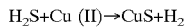

At that time, if the electron density on the $dx^2$-$y^2$ orbid of the cupric ion is large, the above reaction does not proceed well, and if the electron density is small, the reaction proceeds smoothly. The data of the difference of ESR spectrums of cupric ions depending on carriers are shown in the following Table. As will be apparent from the Table, cellulose shows a higher density at $\alpha^2$ than PSS does. It follows that the reaction proceeds easier in the case where the cupric ion is attached to PSS than attached to cellulose.

TABLE (ESR data of a deodorant material supporting cupric ion)

| Polymer | $g_{11}$ | $g_\perp$ | $A_{11}$ | $\alpha^2$ |
|---|---|---|---|---|
| Polystyrene sulfonic acid | 2.2614 | 2.0163 | 0.0112 cm$^{-1}$ | 0.603 |
| Cellulose | 2.3312 | 2.0868 | 0.0112 | 0.703 |
| Polyvinyl alcohol | 2.417 | 2.107 | 0.0112 | 0.798 |
| Polyvinyl pyrrolidone | 2.3950 | 2.1659 | 0.01215 | 0.826 |

5 parts by weight of copper sulfate and 15 parts by weight of sodium polystyrene sulfonate were dissolved in 100 parts by weight of water. A filter paper was immersed in the solution and then dried. $H_2S$ gas having a concentration of 170 ppb was blown through the filter paper at a rate of 5 ml/min. The deodorizing efficiency was 50%.

Comparative Example 3

A filter paper was immersed in a solution of 5 parts by weight of copper sulfate dissolved in 100 parts by weight of water, and then dried. $H_2S$ gas having a concentration of 170 ppb was blown through the filter paper at a rate of 5 ml/min. The deodorizing efficiency was 38%.

As described above, a deodorant material having high efficiency and long lifetime can be obtained by having cupric ion supported on a granular or fibrous active carbon treated by the oxidizing treatment on the acid-attaching treatment. When polystyrene sulfonic acid is used as a carrier for cupric ion, a deodorant material having high efficiency can be obtained.

What is claimed is:

1. A method for deodorizing an air flow containing $H_2S$, comprising deodorizing said air flow by passing it through a deodorant material, said deodorant material comprising (a) a carrier which has been prepared by treating granular or fibrous active carbon by an oxidizing treatment, and (b) cupric ion supported on said carrier, $H_2S$ reacting with said cupric ion.

2. The method of claim 1, wherein said cupric ion is supported in an amount of from 0.01 to 1 mol per mol of said carrier.

* * * * *